United States Patent [19]

Mian et al.

[11] Patent Number: 5,686,271
[45] Date of Patent: Nov. 11, 1997

[54] APPARATUS FOR PERFORMING MAGNETIC CYCLE REACTION

[75] Inventors: Alec Mian, Cambridge; Stephen G. Kieffer-Higgins, Dorchester, both of Mass.

[73] Assignee: Gamera Bioscience Corporation, Medford, Mass.

[21] Appl. No.: 353,573

[22] Filed: Dec. 9, 1994

Related U.S. Application Data

[63] Continuation-in-part of Ser. No. 74,345, Jun. 9, 1994, abandoned.

[51] Int. Cl.$^6$ .................... C19P 19/34; C12Q 1/68; G01N 33/53; C07H 21/04
[52] U.S. Cl. .................... 435/91.1; 435/6; 435/91.1; 435/91.2; 435/7.1; 435/7.2; 435/7.9; 435/5; 435/290; 435/291; 436/135; 436/136; 436/526; 436/531; 536/24.3; 536/24.32; 536/24.33
[58] Field of Search .................... 435/6.5, 91.1, 435/91.2, 5, 7.1–7.9, 290, 291; 436/135, 136, 526, 531; 536/24.3–24.33

[56] References Cited

U.S. PATENT DOCUMENTS 5,401,632  3/1995  Wang et al. .................... 435/6

*Primary Examiner*—Stephane W. Zitomer
*Assistant Examiner*—Dianne Rees
*Attorney, Agent, or Firm*—McDonnell Boehnen Hulbert & Berghoff

[57] ABSTRACT

The invention provides an apparatus for performing a process for amplification of specific nucleic acid sequences based upon the separation of nucleic acid strands by an electromagnetic field. This means of separation allows the use of mesophilic polymerases in the amplification process, thereby increasing the speed and fidelity of the amplification process, as well as the size of target nucleic acid that can be amplified.

4 Claims, 11 Drawing Sheets

COIL DETAIL

WELL A | WELL B

UNLABELLED DNA | 5' RADIOACTIVELY LABELLED DNA

EXTENSION WITH RADIOACTIVE NUCLEOTIDES | EXTENSION WITH NON-RADIOACTIVE NUCLEOTIDES

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AACAGCTATG ACCATG                                                    1 6

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GTAAAACGAC GGCCAT                                                    1 6

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGAACAGGTT ATCGAATTCA GCCAC                                    2 5

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CATCGTCGTG TATTCCGGAC AGTAC 25

APPARATUS FOR PERFORMING MAGNETIC CYCLE REACTION

This application is a continuation-in-part of U.S. patent application Ser. No. 08/074,345, filed on Jun. 9, 1994 now abandoned.

BACKGROUND OF THE INVENTION

1. Field of the Invention

The invention relates to the amplification of specific nucleic acid sequences. More particularly, the invention relates to amplification of such specific nucleic acid sequences using reagents and processes termed herein the magnetic cycle reaction. Specifically, the invention relates to an apparatus for performing such a magnetic cycle reaction to amplify specific nucleic acid sequences in vitro.

2. Summary of the Related Art

The ability to amplify specific DNA sequences has greatly facilitated developments in the fields of molecular biology, medicine and forensics. Early processes for amplifying specific DNA sequences, known as PCR, utilized alternating cycles of thermal denaturation of double-stranded DNA molecules followed by reduced temperature annealing of primers to the single strands and extension of the primers by a polymerase to again yield double strands. Mullis, U.S. Pat. No. 4,683,202 (1987) discloses such a process, in which new polymerase must be added between cycles to replace the polymerase that has been inactivated by the elevated temperatures of the thermal denaturation step. Mullis et al., U.S. Pat. No. 4,683,195 (1987) teaches the use of such a process to detect the presence or absence of a specific nucleic acid sequence in a sample, or to distinguish between different specific nucleic acid sequences in a sample.

These early processes suffered from the considerable inconvenience of having to add polymerase enzyme between cycles. This inconvenience was overcome by the discovery of a purified thermostable DNA polymerase. Gelfand et al., U.S. Pat. No. 4,889,818 (1989) discloses a purified thermostable polymerase enzyme from the thermophilic bacterium *Thermus aquaticus*. Mullis et al., U.S. Pat. No. 4,965,188 (1990) discloses a process for amplifying specific DNA sequences using the thermostable polymerase, thereby eliminating the need to add polymerase between reaction cycles. Johnson et al., U.S. Pat. No. 5,038,852 (1991) discloses an apparatus for automating the polymerase chain reaction using the thermostable polymerase enzyme.

The use of a thermostable polymerase enzyme in a thermal denaturation-based chain reaction has reduced the inconvenience of amplifying specific nucleic acid sequences and has helped the method attain broad commercial acceptance. Unfortunately, the use of the thermostable enzyme, which is made necessary by the thermal denaturation step, has imposed serious limitations upon the amplification process. Foremost among these limitations are the fidelity of the amplification process, the size of the nucleic acid sequence that can be amplified, and the time required to carry out the amplification process. The thermostable polymerase enzyme is more prone to errors in the primer extension reaction than are many known polymerases from mesophilic sources. This can be a considerable problem when the amplification process is used preparatively for cloning. In addition, the thermostable polymerase enzyme has been used successfully to amplify nucleic acid sequences of only about 10 kilobases or less. Finally, the thermostable polymerase enzyme polymerizes deoxyribonucleoside triphosphates at a very slow rate. Coupled with the not inconsiderable time required for the thermal denaturation and annealing steps, this slow polymerization results in an amplification process that is measured in hours.

There is, therefore, a need for processes for amplifying specific nucleic acid sequences that overcome the limitations of the thermal cycle-based processes. Ideally, such a process should decrease the time required for the amplification process as well as the size of the target nucleic acid that can be amplified. Most preferably, such a process should rely upon equipment that is mechanically relatively simple. Such a process is provided by the magnetic cycle reaction, disclosed in co-owned and co-pending U.S. patent application, Ser. No. 08/074,345, filed on Jun. 9, 1994 now abandoned. The achievement of the magnetic cycle reaction has created a need for an apparatus for the efficient performance of such reactions.

SUMMARY OF THE INVENTION

The invention provides an apparatus to enable a process for amplification of specific nucleic acid sequences that is faster than existing methods, has greater fidelity, and can amplify much larger target nucleic acids. This new process is hereby designated "magnetic cycle reaction", or "MCR". The advantages of MCR arise from its use of electromagnetism to effect the strand separation necessary for amplification. Using electromagnetism for strand separation eliminates the need to carry out the amplification process under conditions that destabilize polymerase enzymes. Consequently, the invention provides the convenience of non-stop cyclic amplification of specific nucleic acid sequences without requiring the use of a thermostable enzyme, and instead, mesophilic polymerase enzymes can be used. These mesophilic polymerases catalyze sequence extension at a rate that is at least one and one half orders of magnitude faster than that of the known thermostable polymerases. Moreover, the mesophilic polymerases have much greater fidelity of replication than the thermostable polymerases. In addition, the mesophilic polymerases are far more processive than the thermostable enzymes, allowing the amplification of target nucleic acids up to 100 or more kilobases in length. Thus, the invention provides specific nucleic acid amplification that is faster and more accurate than existing non-stop methods, and that is applicable to much larger target nucleic acid sequences.

The invention provides an apparatus for performing a magnetic cycle reaction, comprising in combination, the following elements:

a temperature-controlled sample block comprising a plate containing an array of a multiplicity of sample tube wells, wherein a portion of a magnetic cycle reaction sample tube fits within the sample tube well, and means for controlling the temperature of the sample block;

a first magnetic element, wherein the first magnetic element is located above the sample block and in proximity thereof, wherein the first magnetic element comprises an array of a multiplicity of coils, wherein the coils comprise a multiplicity of turns of an electricity-conducting wire around a soft iron core, and wherein the flow of electric current through the wire comprising the coil creates a magnetic field surrounding the first magnetic element;

a second magnetic element, wherein the second magnetic element is located beneath the sample block an in proximity thereof, wherein the second magnetic element comprises an array of a multiplicity of coils, wherein the coils comprise a multiplicity of turns of an electricity-conducting wire around a soft iron core, and wherein the flow of electric current through the wire comprising the coil creates a magnetic field surrounding the second magnetic element;

a controller comprising a microprocessor, wherein the controller is operatively linked to the temperature-controlled sample block and each of the first and second magnetic elements, wherein the controller is also operatively linked to a user interface and the controller controls electric current flow through each of the magnetic elements and the temperature of the temperature-controlled sample block; and a power supply that is operatively linked to the controller and supplies electrical power to the apparatus.

In preferred embodiments, each of the magnetic elements comprises an aluminum block containing an array of electromagnetic coils, each coil comprising a soft iron core, wherein each coil is further comprised of a multiplicity of turns of an electrically-conductive wire, around the soft iron core. In a preferred embodiment, each of this multiplicity of coils are placed into a multiplicity of holes into the aluminum block. In further preferred embodiments, the aluminum block is fastened to a soft iron sheet having about the same planar dimensions of the block and affixed along the long surface of the block.

In further preferred embodiments, the temperature-controlled sample block comprises an aluminum block containing a multiplicity of magnetic cycle reaction sample tube wells. In preferred embodiments, the multiplicity of sample tube wells is capable of containing a portion of a magnetic cycle reaction sample tube having a capacity of 1.5 mL, 0.6 mL, 0.2 mL, or any mixture of such sized wells. Additionally, the temperature-controlled sample block is advantageously in thermal contact with heating and cooling means, wherein the heating and cooling means is capable of maintaining a constant temperature in the sample block, within a temperature range of about 1° C., preferably about 0.5° C.

Operation of the apparatus of the invention, and user-mediated operation for magnetic cycle reaction, is provided by a controller comprising a microprocessor. In preferred embodiments, the controller also comprises random access memory (RAM) capability, executable operation files for automatic control of a program of steps comprising, for example, a magnetic cycle reaction, and a user interface for user programming of instructions for the microprocessor. The apparatus also comprises a power supply, wherein alternative current is converted to direct current for supplying appropriate voltages for operation of each of the magnetic elements of the apparatus, as well as operation of the heating and cooling means of the temperature-controlled sample block.

In the methods of using the apparatus disclosed herein, the invention achieves electromagnetic separation of nucleic acid strands by utilizing primer types having two different kinds of bound particles. The first primer type is called "solid phase primer" and has the primer physically bound to a solid phase or immobile particle or surface. The second primer type is called a "magnetic primer" and is actually a primer that is physically bound to a particle that is responsive to an electromagnetic field. In the initial steps of the process according to the invention, the solid phase and magnetic phase primers are incorporated into the target nucleic acid sequences, into strands known as the solid phase strand and the magnetic strand. For single-stranded target sequences, this step requires one round each of polymerase extension from the solid phase and magnetic primers, with a single intervening denaturation step. For double-stranded target nucleic acid sequences, the same initial polymerase primer extension steps are used, but each is preceded by a denaturation step. These steps result in a target nucleic acid that has one end attached to a solid phase (via the 5' end of the solid phase strand) and one end attached to a magnetic particle (via the 5' end of the magnetic strand). Once such a target nucleic acid is obtained, amplification is carried out by multiple cycles of first applying a magnetic field to separate the solid phase and magnetic strands, then allowing additional solid phase and magnetic primers to anneal to the separated strands, then finally carrying out conventional polymerase extension from the annealed primers.

In the performance of a magnetic cycle reaction using the apparatus of the invention, the multiple cycles of amplification are carried out by first applying a magnetic field to each of the samples in the temperature-controlled sample block by generating a magnetic filed in the first, or upper, magnetic element of the apparatus. A magnetic field of sufficient strength is generated by placing a certain voltage of DC current through the electrically-conductive wire comprising the electromagnets of the first magnetic element, to separate the solid phase and magnetic strands. Thereafter, the magnetic field from the first magnetic element is destroyed by halting current flow through the first magentic element. Additional solid phase and magnetic primers are allowed to anneal to the separated strands by applying a magnetic field to each of the samples in the temperature-controlled sample block by generating a magnetic filed in the second, or lower, magnetic element of the apparatus. This magnetic field generated by placing a certain voltage of DC current through the electrically-conductive wire comprising the electromagnets of the second magnetic element, is of sufficient strength to efficiently bring the magnetic primers into proximity with the solid phase-linked DNA template strands. Polymerase-mediated extension of the annealed primers, preferably mediated by a mesophilic polymerase, is allowed in the absence of an external magnetic field, by halting the current in both the first and second magnetic elements. Each of these steps is performed for a time determined to be optimal for denaturation, annealing and extension of the specific nucleic acid to be amplified. Thereafter, cycles of denaturation, annealing and extension are repeated as described until a sufficient amount of the DNA of interest is amplified.

The amplification process facilitated by the apparatus provided by the invention is useful for a variety of purposes. First, the process can be used for diagnostic purposes to determine the presence or absence of a specific target nucleic acid sequence in a sample. In this use, the process according to the invention provides a faster diagnostic approach than existing amplification processes due to the more rapid separation of the target nucleic acid strands and the more rapid polymerization rate of the mesophilic polymerases. Second, the amplification process according to the invention is useful for quantitatively determining the amount of a specific target nucleic acid in a sample, again in a more rapid fashion than is possible with existing amplification processes. The amplification process according to the invention is also useful for preparative uses, such as generating specific target nucleic acid substrates for cloning, sequence analysis and mutagenesis. In this use, the amplification process according to the invention is preferable to existing methods not only due to its greater rapidity, but also because the greater fidelity of the mesophilic polymerases results in fewer mutations in the preparative substrate. In addition, the amplification process according to the invention can be used for nucleic acid mapping, an application that is not possible using existing amplification methods. This use is made possible by the greater processivity of the nucleic acids up to 100 to 200 kilobases in length, compared with the maximum of about 5–10 kilobases obtainable with the less processive thermostable polymerases. This use of the amplification process according to the invention should supplement or replace existing mapping procedures, such as the yeast artificial chromosome cloning approach.

It will also be appreciated that the apparatus provided by this invention is useful in the performance of other amplification-related techniques, including but not limited to ligase chain reaction (LCR), asymmetric amplification of one of a Watson-Crick pair of complementary DNA strands, and DNA cycle sequencing. Additional advantageous uses for the apparatus of the invention will be appreciated by those with skill in this art.

Certain preferred embodiments of the apparatus of the invention, as well as useful embodiments of the magnetic cycle reaction amplification process as facilitated by the apparatus of the invention, are described in greater detail in the following sections of this application and in the drawings.

DETAILED DESCRIPTION OF THE PREFERRED EMBODIMENT

Figure 1A:
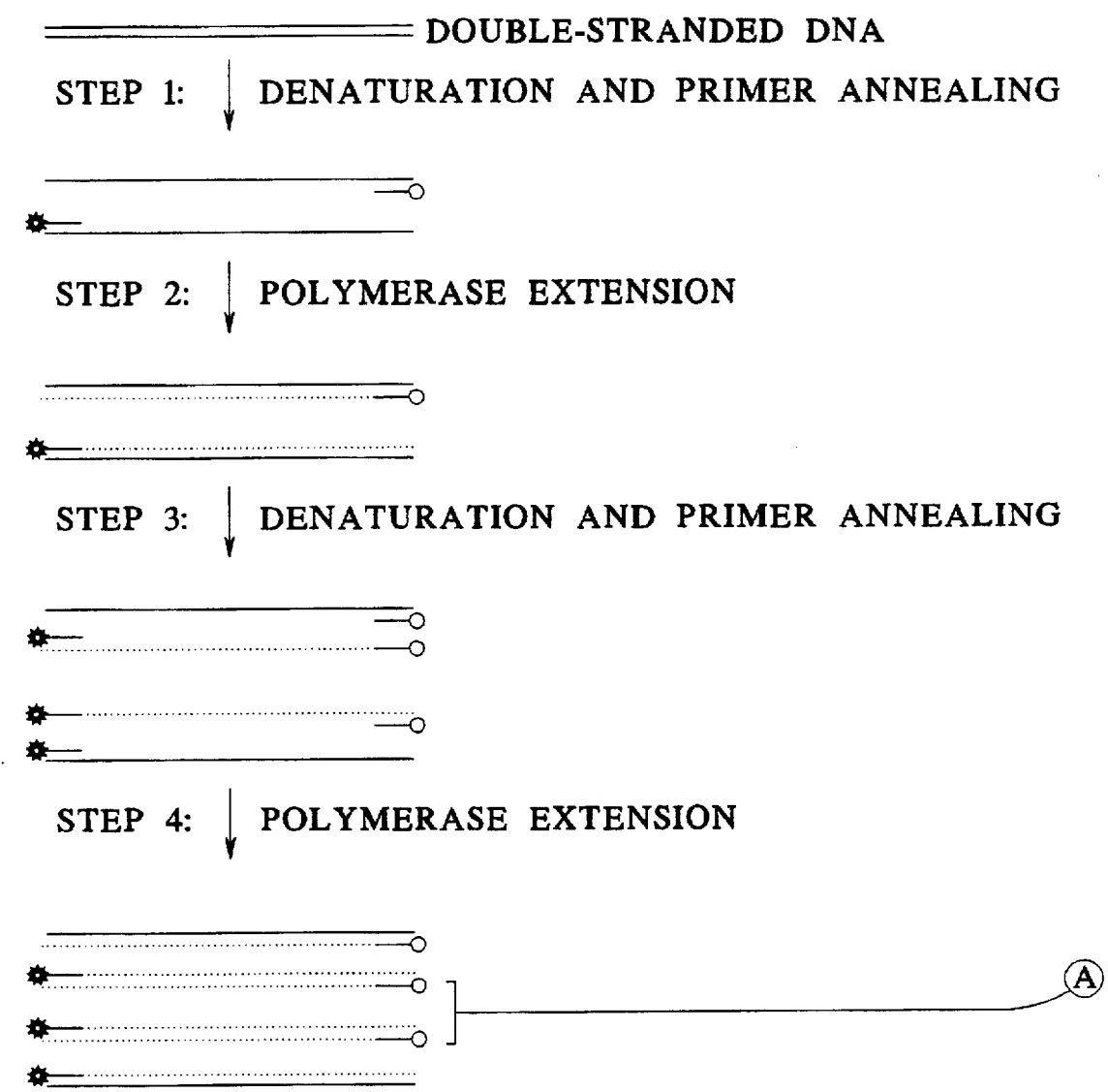
FIG. 1A and 1B are a schematic representation of the basic steps of the magnetic cycle reaction using a double-stranded target nucleic acid. Steps 1 and 2 are denaturation and extension steps. Long solid lines represent the initial target nucleic acid strands. Short solid lines represent primers. Stars and circles at the end of the primers represent attached magnetic particles and solid phase surfaces, respectively. Dashed lines represent primer extension products. Step 5 represents electromagnetic pulse separation of target strands, and is followed by annealing of additional magnetic and solid phase primers and polymerase-mediated extension of the primers.
Figure 1B:
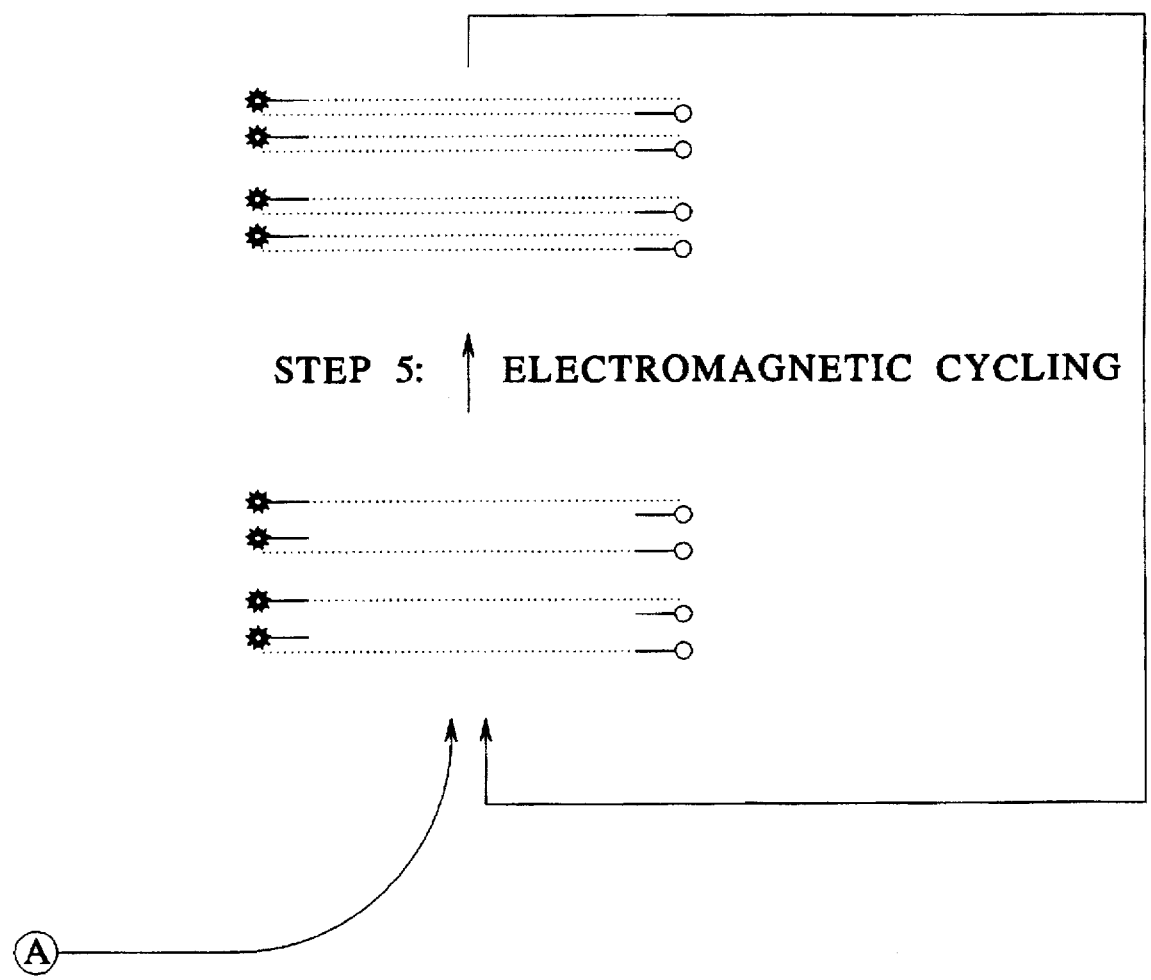

The invention relates to the amplification of specific target nucleic acid sequences. The invention provides new reagents and a new process for carrying out such specific nucleic acid amplification. Specifically, the invention provides an apparatus for performing a method of in vitro amplification of specific nucleic acids termed the magnetic cycle reaction and disclosed herein and in co-owned and co-pending U.S. patent application Ser. No. 08/074,345, filed on Jun. 9, 1993, now abandoned, and incorporated by reference herein.

In the first aspect, the invention provides an apparatus for performing a magnetic cycle reaction. In a second aspect, the invention provides an apparatus for performing a magnetic cycle reaction to amplify a specific DNA fragment. In a third aspect, the invention provides an apparatus for amplifying a specific single stranded target nucleic acid. In a fourth aspect, the invention provides an apparatus for amplifying a specific double stranded target nucleic acid. In a fifth aspect, the invention provide an apparatus for performing a ligase chain reaction. In a sixth aspect, the invention provides an apparatus for performing an asymmetric magnetic cycle reaction of a nucleic acid. In a seventh aspect, the invention provides an apparatus for performing magnetic cycle reaction sequencing of a nucleic acid.

The apparatus of the invention is comprised of each of two magnetic elements, a temperature-controlled sample block, in thermal contact with heating and cooling means, a controller operatively linked to each of the two magentic elements and the sample block, and a power supply. For the purposes of this invention, the apparatus of the invention can be referred to as a "magnetic cycle reaction machine" or "MCR machine", notwithstanding its usefulness for performing other, related in vitro amplification reactions.

The magnetic elements comprising the apparatus of the invention are advantageously comprised of an array of electromagnets, wherein the array comprises between about 1 to about 400 electromagnetic coils. The coils are configured to produce the greatest amount of magnetic field strength. The sum of the magnetic field strength generated by the magnetic coils comprising each magnetic element is capable of generating a sufficient force to separate (denature) a DNA fragment covalently linked to a ferromagnetic bead or particle. This amount of force will be understood from the calculations disclosed below (and in U.S. Ser. No. 08/074,345, now abandoned) to be at least $6.1 \times 10^{-10}$ newtons (N). A preferred embodiment of the magnetic element is a 4×6 array of 24 electromagnetic coils capable of generating about $7 \times 10^{-7}$ N of force.

Each of the magnetic coils is comprised of a soft iron core, wound with an extent of an electrically-conductive wire. Suitable electroconductive wire includes but is not limited to magnet wire having a gauge of between AWG14 to AWG38, most preferably having a gauge of AWG36. An extent of this wire is wound about the soft iron core, wherein the number of windings of wire is from about 50 to about 5000 turns. In a preferred embodiment, the AWG36 wire is wound 1875 times around a 1 cm high×0.5 cm thick soft iron core.

Alternatively, the magnetic elements can comprise a pair of permanent magnets arrayed on top and below the sample block. In such embodiments, a magnetic field is applied to the sample block by moving such a permanent magnet into proximity with the block, and the magnetic field is removed by physically moving the permanent magnet away from the sample block. It will be understood that in such embodiments, means for moving each magnet independent of one another and relative to the sample block, are a component of the apparatus of the invention.

The two magnetic elements are arranged in proximity to a temperature-controlled sample block, wherein one of the magnetic elements, denoted the first magnetic element, is arrayed on top of the sample block, and proximal to the tops of the magnetic cycle reaction sample tubes, and the other magnetic element, denoted the second magnetic element, is arrayed below the sample block, in a position proximal to the bottom of the magnetic cycle reaction sample tubes. The sample block is provided to have approximately equivalent dimensions to each of the two magnetic elements, to provide the maximum uniformity of the applied external magnetic field when current is supplied to the electromagnets. The sample control block can be made of any non-ferromagnetic material, including but not limited to any plastic, glass, or metal, most preferably aluminum. The sample block is comprised of a multiplicity of sample tube wells, typically drilled into one face of the sample block, and arrayed in a regular array across the face of the block. The sample blocks are drilled to dimensions capable of accommodating a multiplicity of sample tubes having a volume of 1.5 mL, 0.6 mL, 0.2 mL or any combination thereof. Alternatively, the sample block can be arrayed to accept a sample pate, for example, a 96-well microtitre plate, or other sample well-containing plate or container.

The sample block is temperature-controlled by the operation of heating and cooling means in thermal contact with the sample block. The temperature of the block is monitored by the controller by feedback control via a thermoelectric means, most preferably a thermistor, capable of conveying temperature information to the controller. Advantageous heating means used to control the temperature of the block include, inter alia, resistive heating elements. Advantageous cooling means used to control the temperature of the sample block include, inter alia, fans and heat sinks, and most preferably, Peltier heat pumps.

The apparatus is monitored and controlled using a controller comprising a programmable microprocessor. Suitable microprocessors include those commercially available from Intel Corporation (such as the 286-, 386-, 486, and most preferably, 586 (known as Pentium) microprocessors), operating at between 25 and 100 MHz. Advantageous controllers also comprise random access memory, in amounts ranging from 4 megabytes (MB) to, most preferably, 64 MB. Suitable controllers of the apparatus of the invention are also provided with a user interface, such as those provided by Omega Engineering Corporation (Stamford, Conn.), to provide complete control over such reaction parameters as temperature, magnetic field strength, number of reaction cycles and duration of each cycle, including the duration of each step of denaturation, annealing and polymerase-mediate extension. The controller is operatively linked to both magnetic elements and to the heating and cooling means of the sample block. The controller is also operatively linked to a power source, which advantageously provides 12V and 5–10A of DC current.

Figure 5:
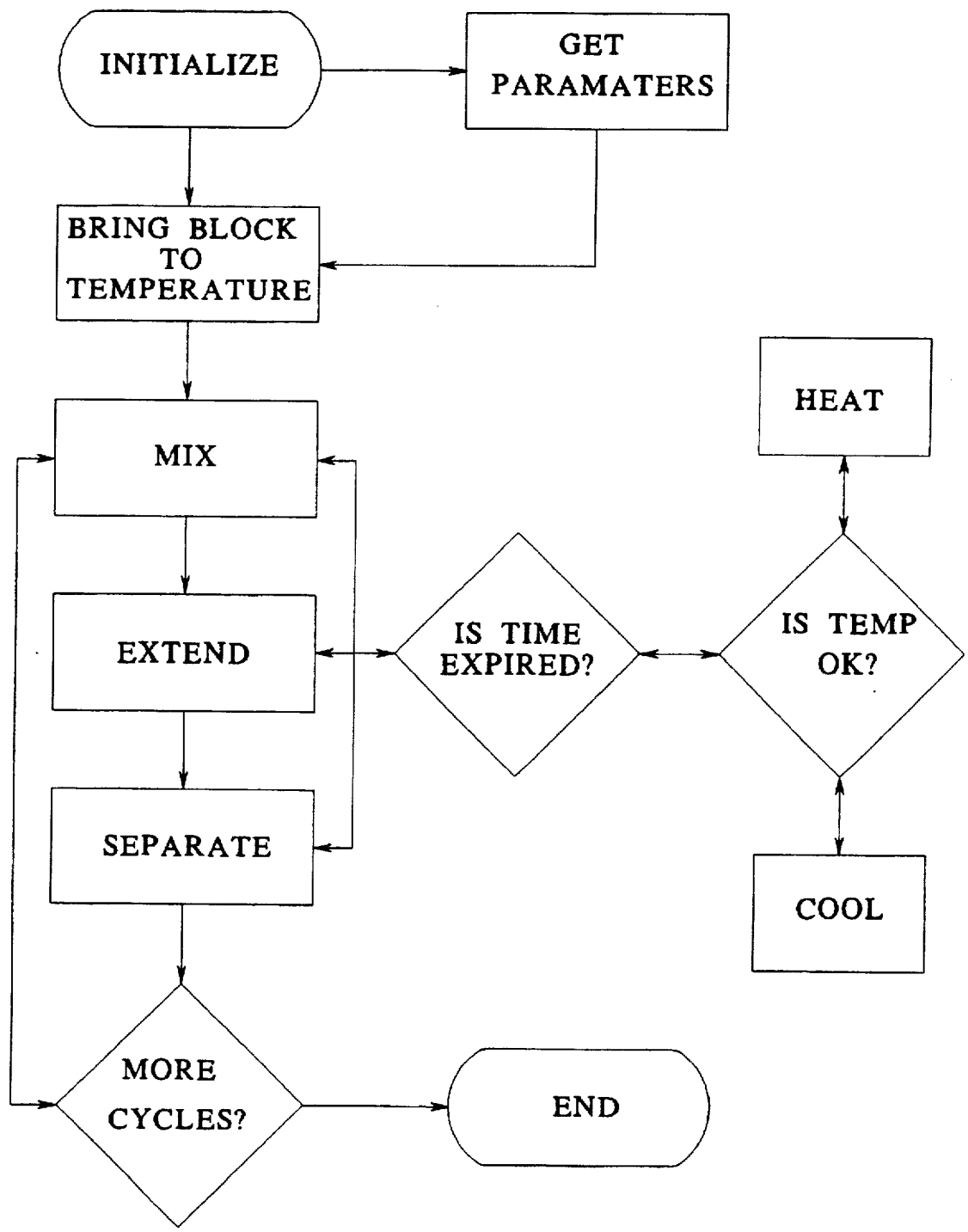
FIG. 5 shows a block diagram of the method of MCR performed by the apparatus of the invention. The controller initializes the system, recovers systems parameters from memory or from the user interface, brings the sample block to a defined temperature, and initiates a series of magnetic cycle reactions comprising mixing, extending and separating in an iterative process, until a defined number of cycles has been achieved. The controller also monitors the duration of each cycle and the component steps of the cycle, controls current flow to the magnetic elements, and monitors the temperature of the sample block and directs the activity of the heating and cooling means to achieve a uniform temperature.

A schematic diagram of a magnetic cycle reaction program is provided in FIG. 5. Each of the steps of the block diagram provides a logic for control of temperature, magnetic field strength and duration of each step of the magnetic cycle reaction.

The invention provides an apparatus that facilitates an improved method for carrying out amplification of specific target nucleic acid sequences that is faster than existing methods, has greater fidelity, and can amplify much larger target nucleic acids. These improvements over existing amplification processes arise from the use of electromagnetism to effect the strand separation necessary for amplification. Accordingly, this new process is designated "magnetic cycle reaction" or "MCR".

The basic steps involved in the MCR process for amplifying a single-stranded target nucleic acid sequence are as follows. First, a solid phase or magnetic primer is incorporated into a nucleic acid strand that is complementary to the target nucleic acid sequence. This step yields a double stranded target nucleic acid that has one strand bound to either a solid phase or magnetic primer, respectively, the solid phase strand or the magnetic strand. Second, the target nucleic acid sequence and its complement are denatured. Third, a magnetic or solid phase primer, whichever was not incorporated into the complementary strand, is incorporated into a nucleic acid strand that is homologous to the target nucleic acid sequence, i.e., complementary to the solid phase or magnetic strand. These steps provide a double-stranded nucleic acid sequence that has one strand bound to a solid phase primer (the solid phase strand) and another strand bound to a magnetic primer (the magnetic strand). Fourth, the two strands are separated from each other by applying a magnetic field, in which the solid phase is immobile and the magnetic strand is mobile. In this step as performed using the apparatus of the invention, the magnetic field is applied by the controller directing current through the coils of the electromagnets comprising the first, or top, magnetic element for a time and at a magnetic field strength sufficient to separate the strands. Fifth, the separated strands are allowed to anneal to additional solid phase and magnetic primers. In this step as performed using the apparatus of the invention, the magnetic field is applied by the controller directing current through the coils of the electromagnets comprising the second, or bottom, magnetic element for a time and at a magnetic field strength sufficient to reassociate the magnetic primers with the solid phase primer-linked template strands. In this step, the solid phase strand is allowed to anneal to a magnetic oligonucleotide primer that is complementary to its 3' end, and the magnetic strand is allowed to anneal to a solid phase primer that is complementary to its 3' end. Sixth, the primers that are annealed to the solid phase strand and magnetic strand are extended by a polymerase to provide additional copies of double-stranded nucleic acids that have one strand bound to a solid phase primer and one strand bound to a magnetic primer. Seventh, steps four through six are repeated as many times as necessary to obtain a desired quantity of nucleic acid copies.

The basic steps involved in the MCR process for amplifying a double-stranded target nucleic acid sequence are the same as for amplifying a single-stranded target nucleic acid sequence, except for the following modifications in the initial steps. Initially, a prefatory denaturation step is necessary to separate the two target nucleic acid strands from each other. Then, the separated target nucleic acid strands are allowed to anneal to primers, with one strand annealing to a solid phase primer and the other strand annealing to a magnetic primer. Next, the primers are extended by a polymerase. These prefatory steps provide two double-stranded target nucleic acids, one of which has one solid phase strand and the other one magnetic strand. The remainder of the process is carried out as described above in steps two through seven for amplification of a single-stranded target nucleic acid.

For purposes of the invention, the term "incorporating a solid phase or magnetic primer into a nucleic acid strand" means hybridizing such a primer to a nucleic acid strand that is complementary to the strand to be synthesized, then extending the primer with a polymerase enzyme in the presence of deoxyribose or ribose nucleoside triphosphates.

For purposes of the invention, the term "magnetic primer" means an oligonucleotide primer that is covalently attached to a particle that is responsive to a magnetic field. Examples of preferred particles for use in such magnetic primers include ferritin molecules and any other metallic particle that is large enough to have a dipole moment, such as DYNABEAD™ paramagnetic beads (Dynel, Oslo, Norway). The particle should be of a sufficient size to impart a maximum force that will separate the strand bound to the particle from a immobile complementary strand attached to a solid phase. For any given particle, the velocity can be determined empirically and maximum force calculated by the Stoke's relation:

$$F_M = 6\pi n r v$$

where r is the particle's radius, n is the viscosity of the buffer used for amplification and v is the unbound particle's measured velocity through the buffer. For purposes of the invention, the term "solid phase primer" means an oligonucleotide primer that is attached to a solid or immobile phase. In a preferred embodiment the solid phase is controlled pore glass (CPG) and the primer is covalently attached to the solid phase in the conventional manner used for synthesizing oligonucleotides. in another preferred embodiment, the primer is indirectly attached to the solid phase via a receptor-ligand interaction. In this embodiment, a receptor is covalently attached to a solid phase and its ligand is covalently attached to the primer, or vice versa. Thus, the primer becomes bound to the solid phase through the non-covalent receptor-ligand binding. Since binding to the solid phase should be very strong, the receptor-ligand affinity should be very high, such as that of the avidin-biotin system, which as an affinity of about $10^{15}$/mole. Primers according to the invention are preferably covalently attached to the magnetic particle, solid phase surface, receptor, or ligand. Such attachment may be by a variety of mens, and in a preferred embodiment involves the 5' hydroxyl group of the oligonucleotide. The length of the primers is generally the ordinary length for primers used in well-known polymerase chain reaction, and preferably is from about 8 to about 50 nucleotides. For purposes of the invention, a "magnetic strand" is a nucleic acid strand having an incorporated magnetic primer and a "solid phase strand" incorporated solid phase primer.

In the method according to the invention, the denaturation of double-stranded target nucleic acid prior to incorporation of both solid phase and magnetic primers may be carried out in a variety of ways. In one preferred embodiment, such denaturation can be achieved thermally, for example, by subjecting the sample to a temperature of 94° C. for abut one to about five minutes, preferably for about 2 minutes. In an alternative embodiment, such denaturation can be achieved by exposure of the sample to base, preferably at a pH of from about 13 to about 14. In the first case, subsequent annealing of the solid phase or magnetic primers to the separated strands is achieved by lowering the temperature to below the Tm, usually from about 45° C. to about 65° C. for up to 5 minute sin the presence of excess primer. In the second case, annealing is carried out in the presence of excess primer by bringing the sample to neutral pH, preferably from about pH 7 to pH 9. In either case the molar excess of primer over target nucleic acid is preferably about $10^3$-fold for cloned target nucleic acids and about $10^6$-fold for genomic target nucleic acids, and most preferably with a primer concentration of about 100 picomoles per reaction. In either case, an appropriate polymerase enzyme is then added in the presence of deoxyribonucleoside or ribonucleoside triphosphates. Appropriate polymerases include any RNA or DNA polymerase from any eukaryotic or prokaryotic organism or virus. Preferred polymerases include T7 DNA polymerase and the E. coli DNA polymerase holoenzyme or Klenow fragment. Preferably, the nucleoside triphosphates are deoxyribonucleoside triphosphates and are present at the concentration of about 100–300 μM for each dNTP. Most preferably the primer extension takes place in a buffer also containing about 5–15 mM $Mg^{2+}$, 1 mM dithiothreitol (DTT), 0.5 mM each of solid phase and magnetic primers, 0–5 mM betaine, and having a pH of about 7–8 due to the presence of about 10–20 mM Tris-HCl or HEPES buffer at that pH.

Figure 2A:
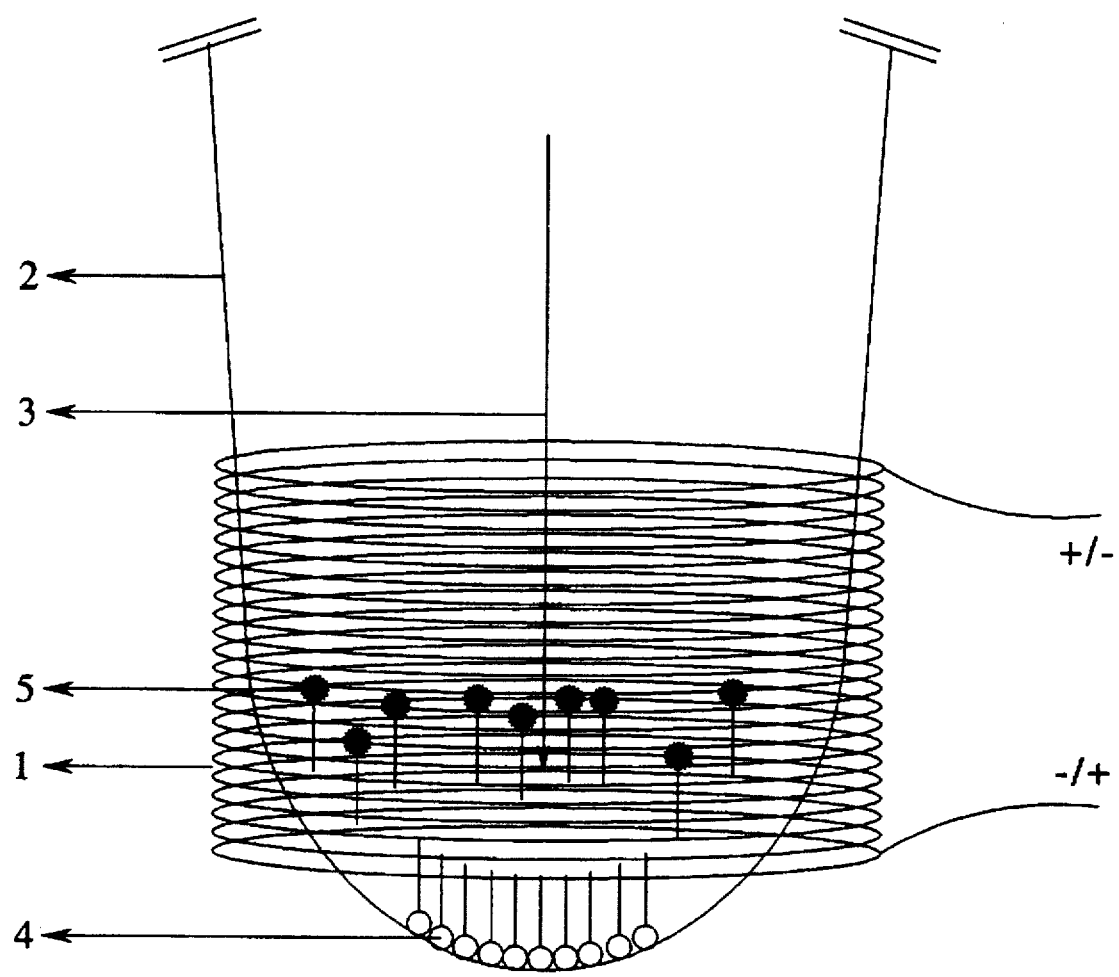
FIG. 2A and 2B show a general schematic representation of how the electromagnetic separation of the magnetic particle-bound and solid phase-bound target strands is achieved. A solenoid, 1, is wrapped around a test tube, 2, in which the amplification process takes place. Application of an electric pulse through the solenoid in one direction creates a magnetic field in the direction of the long arrow, 3. Attachment of one target strand to the solid phase surface, 4, prevents mobility of that strand in response to the magnetic field. In contrast, the other target strand is separated from the first target strand by the magnetic field due to its attachment to a magnetic particle, 5. Reversal of the electric pulse creates a magnetic field in the opposite direction, represented by the short arrow, 6, which returns the magnetic particle-bound strands and primers, 7, to the vicinity of the solid-phase bound target strands.
Figure 2B:
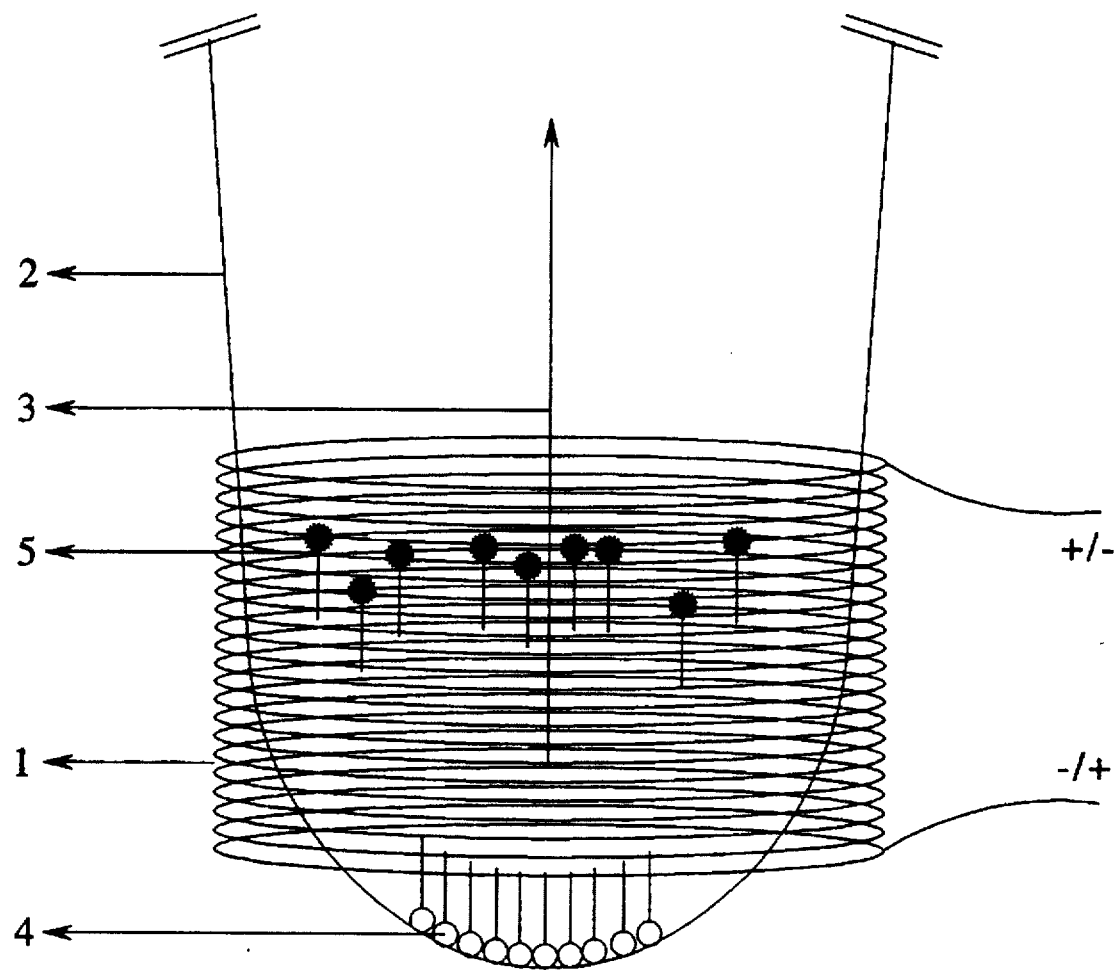

Once a solid phase primer has been incorporated into one strand of the target nucleic acid and a magnetic primer has been incorporated into the opposite strand, all further stand separation steps can be undertaken by application of an electromagnetic field. As shown in FIG. 2, attachment of one strand to a solid or immobile phase and pulling of the other strand by an electromagnetic force results in disruption of the base stacking and hydrogen bonding interactions between the strands, culminating in strand separation. The electromagnetic force applied to the double-stranded target nucleic acid should be sufficiently strong to disrupt the base stacking and hydrogen bonding interactions between the strands, but not so strong as to disrupt covalent bonding interactions within the individual strands.

The force necessary to break the weakest intrastrand bond in a DNA molecule is about 368,000 joules/mole, or about $6 \times 10^{-19}$ joules/molecule. Since work (W)=force (F)× distance (D), then the minimum force necessary to cause intrastrand scission is F=W/D. For DNA, the distance through which the force acts is $3.3 \times 10^{-10}$ meters/molecule (see Smith et al., 1992, *Science* 258:1122–1126). Thus, the minimum strand scission force, $$F_S = \frac{6 \times 10^{-19} \text{ j/molecule}}{3.3 \times 10^{-10} \text{ m molecule}} =$$

$$1 \times 10^{-9} \text{ joule/mole} = 1 \times 10^{-9} \text{ Newton(N)}.$$

In contrast, the force necessary to disrupt a DNA duplex molecule is based upon the principal equation:

$$2f/[1-f]^2 \, C_o = \exp(-\Delta G^\circ / RT),$$

where $C_o$=concentration of single-stranded DNA;

f=0.9 when T=$T_{90}$ (90% dissociated temp.);

f=0.5 when T=$T_{50}$ (50% dissociation temp.=$T_m$);

and f=0.1 when T=$T_{10}$ (10% dissociation temp.).

The temperature dependence of $\Delta G$ follows the integrated form of the Gibbs-Helmholtz equation:

$$\Delta G = -T\Delta S + \Delta H.$$

Thus, for a 200-mer, $\Delta G^\circ$=31.4–$\Delta G$+(initiation energy)=26.5 kcal/mole $\Delta S^\circ$=0.32928 kcal/mole $\Delta H^\circ$=148.8 kcal/mole and $\Delta G_{90} - \Delta G_{10}$=31 kcal/mole, or about $2 \times 10^{-19}$ joules/molecules.

Thus, $$F_D = \frac{2 \times 10^{-19} \text{ joules/molecule}}{3.3 \times 10^{-10} \text{ m/molecule}} = 6.1 \times 10^{-10} \text{ N}.$$

According to these value, the dissociation force, $F_D$, does not approach the scission force, $F_S$, until the duplex to be dissociated reaches about 600 b.p. At well below this size range, however, duplex dissociation becomes cooperative, allowing complete dissociation without ever reaching $F_S$.

As indicated, it is beneficial to carry out dissociation at a temperature near the $T_m$ of the duplex. However, the dissociation should occur at a temperature that does not destabilize the polymerase enzyme used for primer extension. Accordingly, it is preferable to use agents that lower the $T_m$ of the duplex. For example, the zwitterion betaine, at >5M concentration, shifts the melting temperature of calf thymus DNA from about 62° C. to about 48° C., without affecting protein-DNA interactions at neutral pH. Thus, in a preferred embodiment, MCR is carried out in a buffer containing >1M betaine, most preferably from about 5.2M to about 5.6M betaine. Alternatively, melting temperature can be reduced by the presence of about 2.4M triethyl-ammonium chloride. It should be noted that the use of such agents to reduce melting temperature is generally more desirable when either longer target nucleic acids or target nucleic acids having higher G+C content are involved. Further destabilization of the double helix can be achieved by the addition of single strand binding (ssb) proteins, such as *E. coli* ssb, and/or helicases, such as *E. coli* DNA helicases I, II, and IV (see Wood and Matson, 1987, *J. Biol. Chem.* 262:152–169 and 1989, *J. Biol. Chem.* 264: 82–97). Other chemicals denaturants can also be added in limited quantities to further reduce melting temperature. These denaturants include lower alkyl (1–4 C) alcohols, urea, formamide, and other hydrogen bond competitors. When such chemical denaturants are used, care must be taken to use them in quantities that will not excessively destabilize the polymerase enzyme. Such agents, used properly, can actually have the opposite effect. For example, 10% ethanol actually stabilizes the polymerase enzyme. The combination of various hydrogen bond destabilizing agents in the MCR reaction buffer allows the melting temperature of the target nucleic acid to be reduced such that the MCR can be carried out at a temperature just below the DNA melting temperature, but at which mesophilic polymerases remain stable and active. Carrying out MCR under these conditions ensures that the force required to separate the target nucleic acid strands is well below that level at which intrastrand covalent bond scission occurs.

In another aspect, the invention provides an apparatus for rapid quantitative assay for determining the abundance of a specific target nucleic acid in a sample. Such quantitative assays are well known for use with the polymerase chain reaction. (See e.g., Noonan et al., 1990, *Proc. Natl. Acad. Sci. USA* 87:7160–7164). The method according to the invention, MCR, can simply be used in place of PCR in the well known quantitative assay that can be carried out in considerably less time than existing assays, due to the speed of MCR, relative to PCR.

In yet another aspect, the invention provides an apparatus for an improved process for preparative generation of substrate nucleic acid molecules for cloning, sequence analysis, or mutagenesis. The method according to the invention provides such substrates having fewer mutations than those produced by current amplification procedures, due to the greater fidelity of the mesophilic polymerases. Consequently, the method according to the invention provides more reliable substrates for subsequent molecular biology manipulations.

In still an additional aspect, the invention provides an apparatus for facilitating long range genomic mapping. This is made possible by the ability of mesophilic polymerases to amplify target nucleic acids in the 100 to 200 kilobase size range. Currently, mapping over this size range can be carried out only by the somewhat cumbersome cloning of DNA into yeast artificial chromosomes (YACs). The ability to amplify such large target nucleic acid regions, however, provides a simpler approach. As sequence tag sites (STSs) are identified within the genome at 50–100 kb intervals (see, e.g. Olson et al., 1989, *Science* 245:1434–1435), the regions between consecutive STSs can conveniently be amplified by the method according to the invention, thereby providing a substrate for more fine-scale mapping by conventional procedures.

The following examples are intended to further illustrate certain preferred embodiments of the invention and are not limiting in nature.

EXAMPLE 1

Determination of the Actual Maximum Force Provided by a Particular Magnetic Particle In An Electromagnetic Field Dynabead™ paramagnetic beads are obtained from Dynal, Oslo, Norway. The maximum magnetic force acting on the bead is determined by measuring the bead's velocity when traveling through a buffering a microchamber in response to an electromagnetic field. The microchamber is constructed from a glass slide and sealed coverslip, with the volume between the two occupied by MCR buffer (see Example 4, below). The bead is placed at one end of the sealed, fluid-filled chamber. The slide is then surrounded with a solenoid through which current is passed to create the electromagnetic field. A computer cursor is superimposed on the microscope image and used to record the bead's velocity. since there is variation between beads, this measurement is taken for several beads. Velocity measurements are made for field strengths that theoretically impose a force upon the bead of $10^{-10}$, $5 \times 10^{-9}$, $10^{-8}$, $5 \times 10^{-8}$, $10^{-7}$ and $5 \times 10^{-7}$ Newtons. The actual maximum force for the average of several beads is then determined by averaging the observed velocities of the beads and applying the Stokes' relation $$F_M = 6\pi n r v$$

where r is the bead's radius, n the buffer viscosity, and v the bead's velocity. This value is then compared with the theoretical force that the electromagnetic field should have imposed upon the beads, and is thus used to calibrate the electromagnetic field to be used in each of the following examples.

EXAMPLE 2

Determination of the Minimum Force Required to Cause Intrastrand Covalent Bond Scission Prior to removal of the 5' dimethoxytrityl (DMT) group, a 50-mer oligodeoxynucleotide is biotinylated at its 3' hydroxyl by standard procedures. The DMT group is then removed in aqueous acetic acid and the oligonucleotide purified on $C_{18}$ HPLC. A glass microscope slide is coated with alkylamidopropanoic acid according to standard procedures. The biotinylated oligonucleotide is then esterified directly to the carboxyl moiety of the alkylamidopropanoic acid. Next, avidin conjugated DYNABEAD™ paramagnetic beads are added to the objective portion of the slide and unbound beads are rinsed away. The objective portion of the slide is then flooded with MCR buffer (see Example 4) and a coverslip is added. The slide is wrapped in a solenoid, and an electromagnetic field of appropriate strength to generate an actual force of $10^{-10}$N on each bead is generated by directing electrical current through the solenoid. The actual force is increased until the oligonucleotides undergo scission at a force of about $10^{-9}$N.

$$F = W/D = \frac{6 \times 10^{-19} \text{ j/molecule (for lowest bond dissociation energy in DNA)}}{3.3 \times 10^{-10} \text{ m (maximum extension of single internucleotide linkage)}}$$

Therefore, $F = \sim 2 \times 10^{-9}$ joule/molecule $= \sim 2 \times 10^{-9}$ N.

EXAMPLE 3

Determination of the Minimum Force Necessary for Destabilization of an Oligonucleotide Double Helix A 3' levulinyl oligonucleotide (50-mer, same as in Example 2) is esterified directly via its 5' hydroxyl to the carboxyl group of alkylamidopropanoic acid coated glass microscope slide. The levulinyl protective group is then removed in base. A 5'-paramagnetic bead-derivatized 50-mer oligonucleotide having its 10 most 3' nucleotides complementary to the 10 most 3' nucleotides of the glass-bound oligonucleotide is then added in MCR buffer containing T7 DNA polymerase (see Example 4). Extension of the oligonucleotide produces a 90-mer duplex. A coverslip is added and the microscope slide is wrapped in a solenoid and placed on a microscope stage. Electrical current is then directed through the solenoid to generate an actual force upon the parmagnetic beads of about $10^{-10}$ N. This force is gradually increased until the strands of the duplex are separated at a force of about $6.1 \times 10^{-10}$ N.

EXAMPLE 4

Demonstration of Strand Separation using Electromagnetic Force

The ability of a force generated by an applied electromagnetic field having field strength generated by the MCR apparatus described above to separate the strands of a 750 bp double-stranded DNA molecule was determined. Additionally, the assay used for this determination was also used to detect whether any strand scission accompanied DNA duplex denaturation.

Figure 6:
FIG. 6 shows the experimental scheme used in the experiments described in Example 4. The Figure shows two representative wells of type A (well A) and B (well B) onto each of which a plurality of 750 nucleotide single-stranded DNA molecules have been covalently attached at the 5' of each DNA molecule. The DNA molecules in wells B are radioactively labeled (indicated by an asterisk), while those of wells A are not. In the second step of the experimental protocol, a plurality of 500 nucleotide single-stranded DNA molecules complementary to the 3' extent of the covalently-attached 750 nucleotide DNA molecules are annealed to the 750 nucleotide DNA molecules in each of the wells A and B. The 500 nucleotide DNA molecules are biotinylated at their 5' ends, and non-covalently attached to streptavidin-coated magnetic beads. These DNA molecules are then extended using T7 DNA polymerase in step 3 of the protocol in the presence (wells A) or absence (wells B) of radiolabeled nucleotide precursors. In step 4, the two DNA strands are separated at 50° C. by the application of an external magnetic field, and the separated, extended, magnetic bead-linked strands isolated for electrophoretic analysis. After this separation, the wells were eluted at 90° C. and DNA recovered for electrophoretic analysis.
Figure 6:
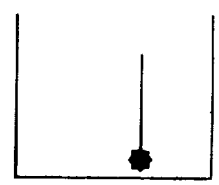
Figure 6:
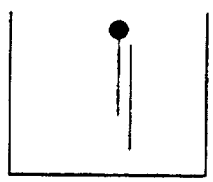
Figure 6:
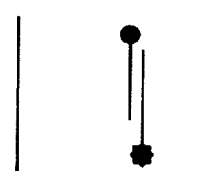
Figure 6:
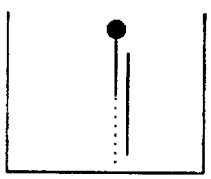
Figure 6:
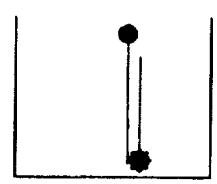
Figure 6:
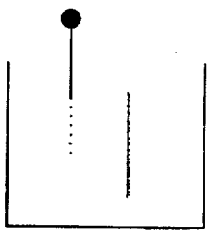
Figure 6:
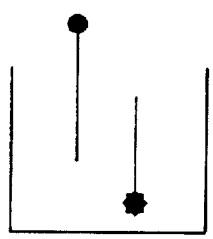
Figure 6:
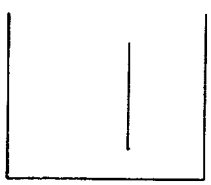
Figure 6:
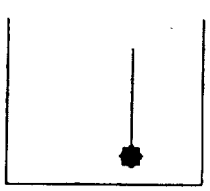

The experimental scheme for this assay is shown in FIG. 6. Two types of microtitre wells were prepared. In both wells, about 0.2 picomole of a 750 nucleotide, single-stranded DNA fragment was covalently linked to the microtitre well. In wells A, this DNA fragment was unlabeled, while in wells B the DNA fragment was radioactively labeled at its 5' end. Each of the 750 nucleotide fragments in these wells was annealed with a 500 nucleotide, single-stranded DNA molecule complementary to the 3' 500 nucleotides of the 750 nucleotide fragment. The 500 nucleotide fragment was biotinylated at its 5' end and non-covalently linked to streptavidin-coated magnetic beads. T7 DNA polymerase was added in the presence of appropriate buffers, salts and dNTPs and the 500 nucleotide fragment was extended. In wells A, extension was performed in the presence of ($^{32}$P)-labeled dCTP, while in wells B no radioactive dNTPs were present. After extension, the extended strands were separated by the application of an external magnetic field as described above at 50° C. The extended product was then eluted from the Dynabeads with a formamide solution as in Example 7 below and analyzed by electrophoresis. The wells are then heated to 90° C. and the resulting supernatants also analyzed electrophoretically.

Figure 7:
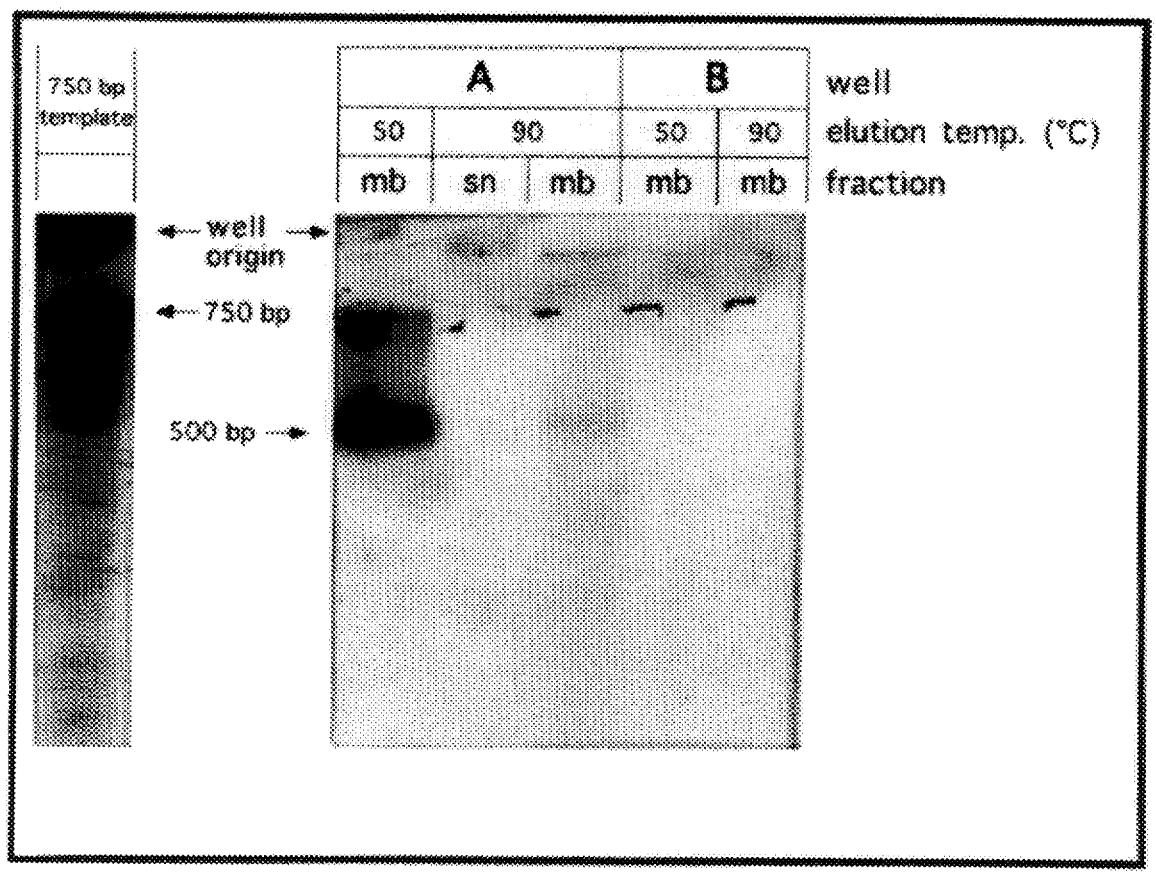
FIG. 7 shows the results of electrophoretic analysis of the DNA fragments produced according to Example 4. The first electrophoretic pattern on the left was produced by electrophoresis of radiolabeled 750 nucleotide template DNA and is shown as a control. The positions of the electrophoretic well origin, and of the 750 and 500 nucleotide DNA fragments, are indicated by arrows. The electrophoretic patterns of the DNA recovered by magnetic strand Separation (50° C.) and thermal denaturation (90° C.) from each of the wells A and B are shown.

The results of these experiments are shown in FIG. 7. A sample of the radiolabeled 750 nucleotide template is shown for comparison. In the samples from wells A, radiolabeled (extended) DNA is seen in a broad smear from 500–750 nucleotides, representing the population of DNA molecules extended to varying extents. Further thermal denaturation at 90° C. shows essentially no additional radiolabeled DNA, indicating that magnetic separation was quantitative in these experiments. Wells B show no radiolabeled DNA at either 50° or 90° C., indicating that magnetic separation was achieved without significant strand scission, and that covalent attachment of the radiolabeled template strand is stable to heating at 90° C.

These results demonstrate that DNA fragments at least 750 nucleotides in length can be quantitatively separated using an external magnetic field without concomitant strand scission, as predicted from the theoretical discussion presented in Examples 1–3.

EXAMPLE 5

An Apparatus for Performing Amplification of a DNA Sequence using MCR

Figure 4A:
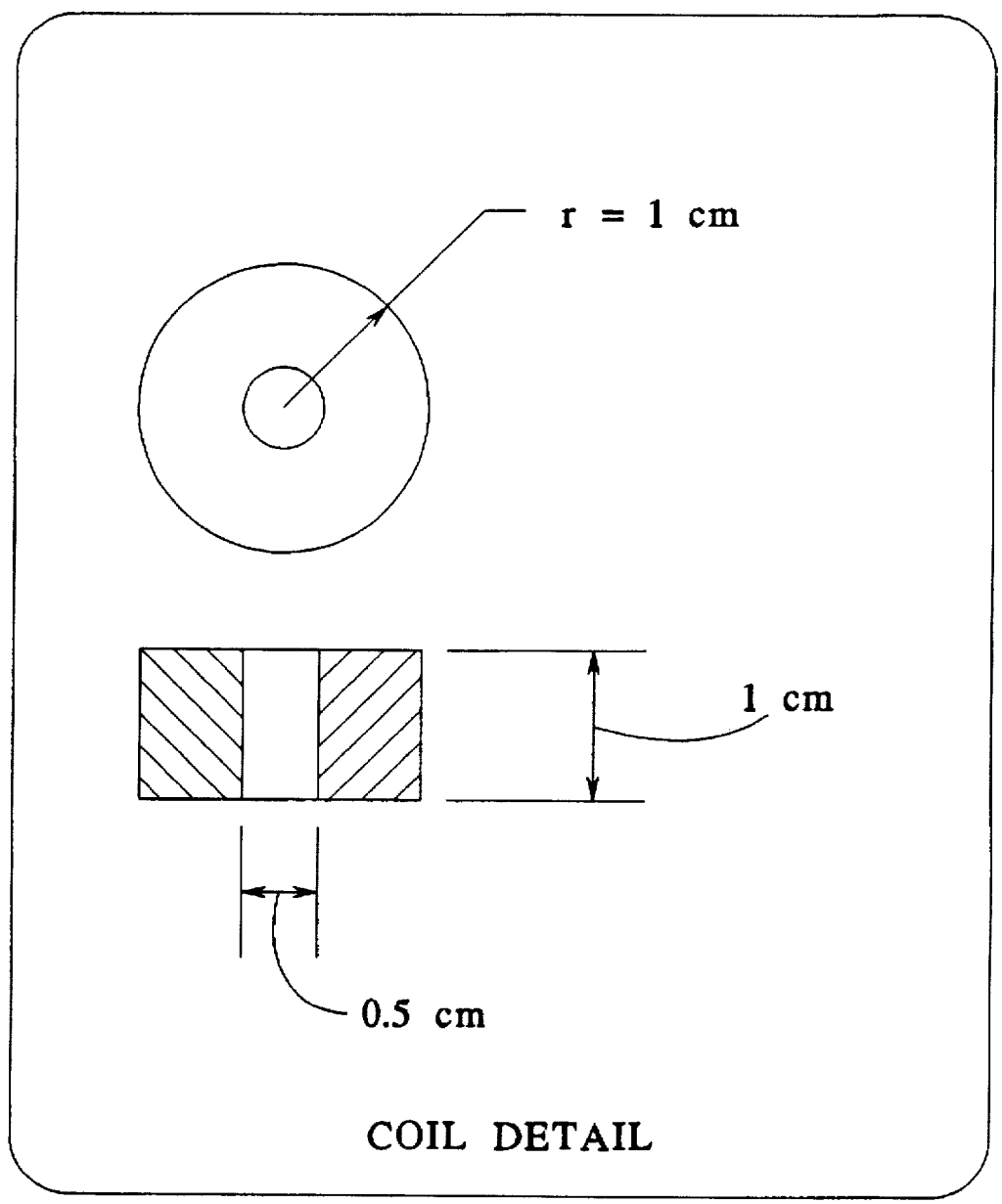
FIG. 4A and 4B represent a diagram of each of the magnetic elements comprising the apparatus of the invention. Panel 4A illustrates the dimensions of a preferred embodiment of an electromagnetic coil comprised of a soft iron core wound with 1875 wrappings of AWG36 magnet wire. Panel 4B illustrates the dimensions of a 4×6 array of 24 electromagnetic coils in a 13 cm×9 cm×1.25 cm aluminum block.
Figure 4B:
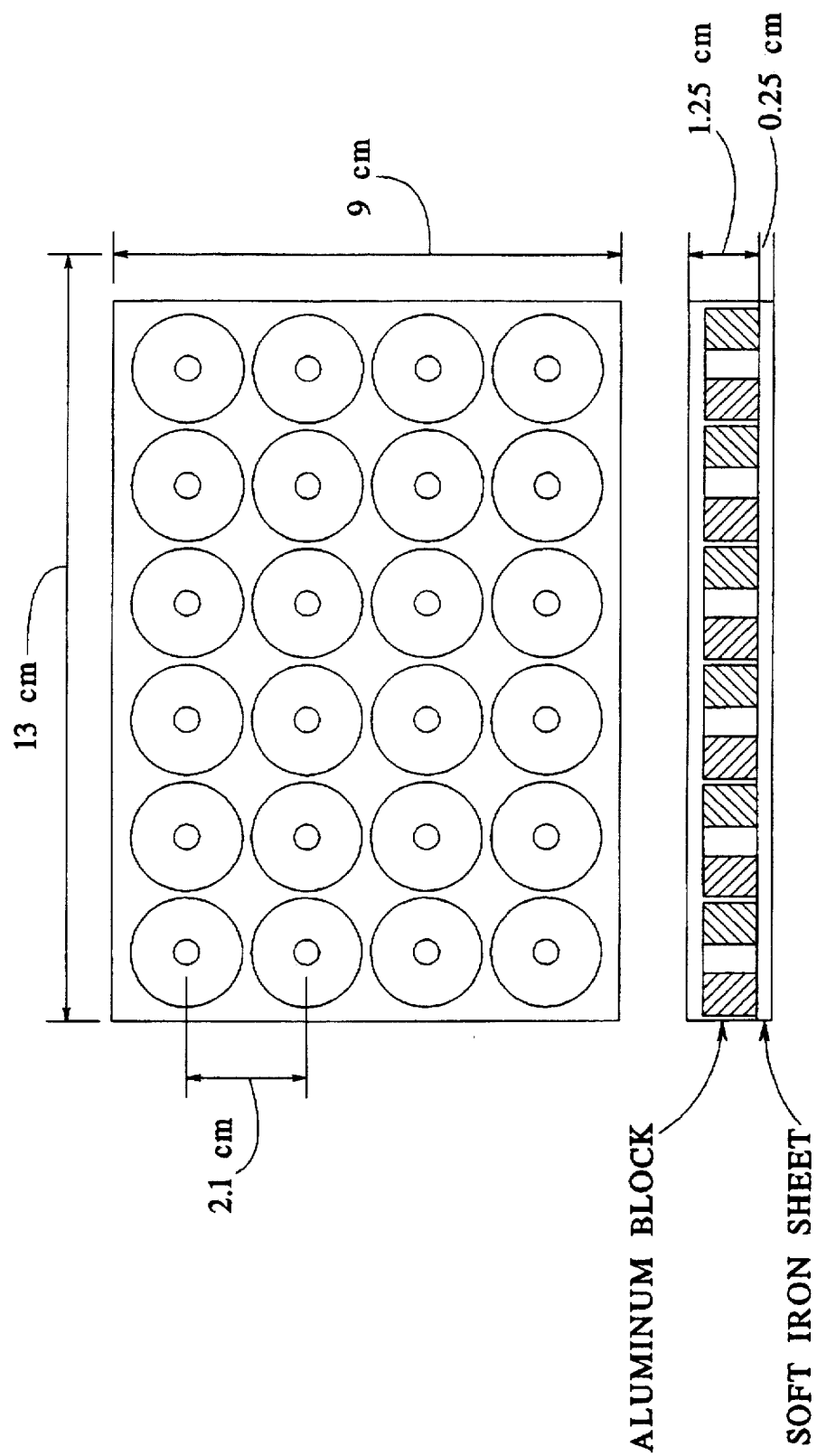

An MCR apparatus is constructed as follows. Each of two magnetic elements are constructed from a 13 cm×9 cm×1.25 cm cast aluminum block. Into this block are milled a 4×6 array of 24 holes having dimensions of about 1 cm deep and 2 cm in diameter, wherein the center of each hole is separated from each of its neighbors by about 2.1 cm. This arrangement is illustrated in FIG. 4A and 4B. Into each of these holes in placed an electromagnetic coil element constructed as follows. A soft iron core, having dimensions of about 1 cm×0.5 cm, is wound with about 1875 turns of 36 AWG magnet wire to give a coil having final dimensions of 1 cm height×2 cm diameter. After placement of the coils, the block is fastened along one side to a 13 cm×9 cm×0.25 cm soft iron sheet.

It is calculated, using the equation:

$$B=n(2\pi k'I/r)$$

where B is the magnetic flux in tesla
I is the current in amperes (A)
n is the number of turns in the electromagnet
k' is a proportionality constant=$10^{-7}$ tesla-meters/amperes
r is the radius of the coil in meters that for a current (I) of 50 milliamperes (mA), each one of the coils of the invention generates a magnetic field of about $5.9 \times 10^{-3}$ tesla.

It is further calculated, using the equation:

$$F=B(I)(l)$$

where F is the force in newtons
B is the magnetic flux in tesla
I is the current in amperes (A)
l is the length of the coil in meters that the 24-coil array described above will generate a force of about $7 \times 10^{-7}$ newtons.

Each of the magnetic elements described above is placed in operative proximity to a temperature-controlled sample block, constructed as follows. The sample block is constructed of cast aluminum, and comprises an array of between 24 and 96 magnetic cycle reaction sample tube wells, evenly distributed on one surface of the aluminum block. These sample tube wells are constructed to hold a plurality of sample tubes having a capacity of 1.5 mL, 0.6 mL or 0.2 mL; the size of each sample tube well at least partly determines the size of the sample block. The sample block of this apparatus has dimensions of about 13 cm×9 cm×6 cm. The block is kept at a constant temperature using feedback control monitored by the controller. To this end, the block is in thermal contact with an embedded platinum thermistor, which is operatively linked to the controller. The block is also in thermal contact with a series of three 12V DC resistive heating elements. Forced air cooling of the block is provided by a 12V DC fan and heat sinks, or by Peltier heat pumps in thermal contact with the sample block and operatively linked to the controller. The controller is programmed to prevent simultaneous activation of both heating and cooling elements.

The controller is a Packard Bell Pentium/60 MHz computer equipped with 8 megabytes of random access memory (RAM) and a 420 MB hard drive programmed using Microsoft Basic software. The computer monitors and controls the other components of the system using an Omega OM-900 interface (Omega Engineering, Stamford, Conn.), specifically using the following modules: OM-991 CPU using an 8088 processor; OM-932 RTD input module; OM-911 general purpose input/output (I/O) module; and a OM-903 power supply. The program is configured to provide the user with control over the operating temperature, the number of magnetic reaction cycles, the duration of each cycle, and the duration (time) of each of the denaturation, annealing and extension steps of each cycle. In constructing the apparatus as described herein, the controller is operatively linked to each of the magnetic elements, the heating and cooling elements of the temperature-controlled sample block, and the power supply.

The apparatus is powered using a 12V, 5A DC power supply operatively linked to the controller.

Figure 3A:
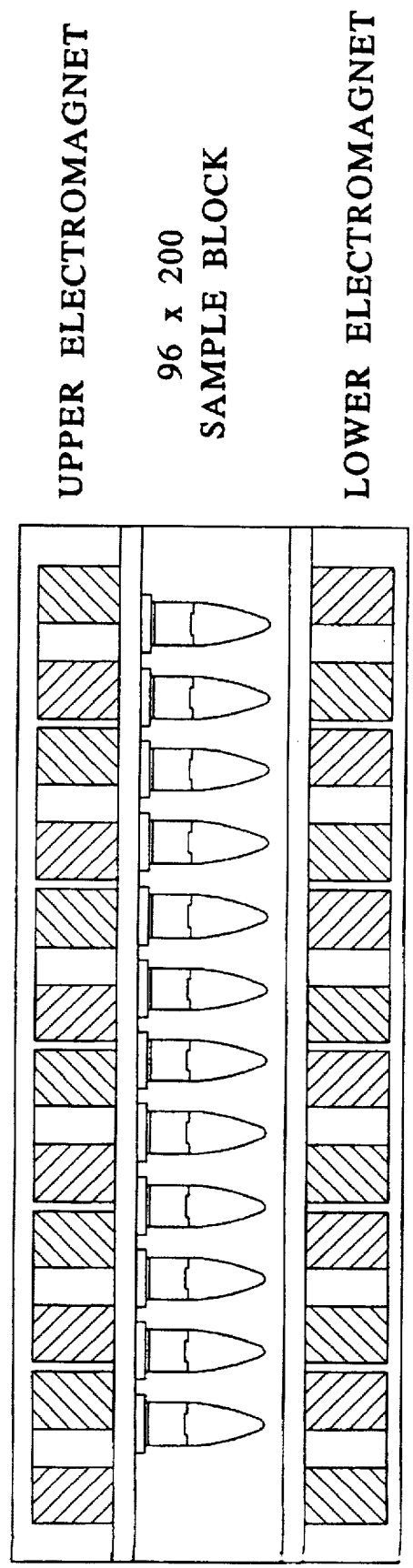
FIG. 3A and 3B show a block diagram of the apparatus of the invention. Panel 3A illustrates the arrangement of each of the two magnetic elements with relation to a temperature-controlled sample block. Panel 3B illustrates the operative connections between each of the components of the apparatus of the invention.
Figure 3B:
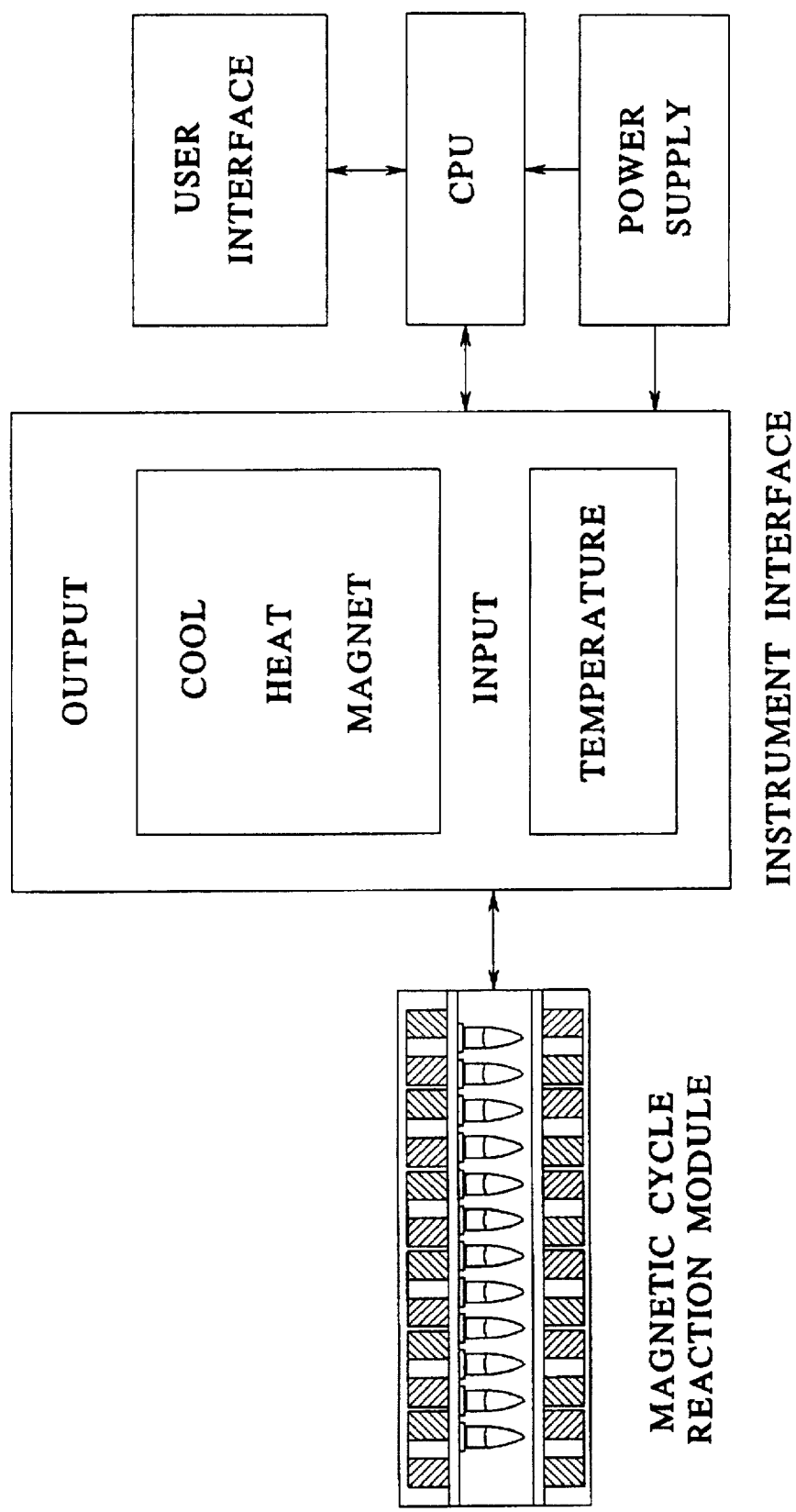

The arrangement of the components of the apparatus of the invention is illustrated in FIGS. 3A and 3B.

EXAMPLE 6

Amplification Protocol for Amplifying a Target DNA Sequence using MCR

The pBluescript™ SK+1- vector is linearized with PvuII and a 210 b.p. fragment spanning the polylinker is amplified as follows. One ng digested plasmid is added to an Eppendorf tube containing a solution containing 15 mM Tris-HCl (pH 7.5), 10 mM MgCl, 1 mM dithiothreitol (DTT), 0.2 mM dNTPs, 0.5 mM solid phase primer and 0.5 mM betaine.

The solid phase primer is 5'-AACAGCTATGACCATG-3' (SEQ ID No.:1), with the 5' hydroxyl group esterified to the carboxyl group of alkylamidopropanoic acid-controlled pore glass. The magnetic primer is 5'-GTAAAACGACGGCCAT-3' (SEQ ID No.:2), with the 5' end biotinylated and linked to a streptavidin-derivatized DYNABEAD™. The solution is heated to 97° C. for 2 minutes, then allowed to cool to 50° C. Ten units of T7 DNA polymerase is then added and the solution is incubated at 45° C. for 2 minutes. The solution is heated to 97° C. for 2 minutes, then again cooled to 50° C. Ten units of T7 DNA polymerase is added and the solution is again incubated at 45° C. for two minutes. The solution is transferred to an MCR machine, with the eppendorf tube fitting within a solenoid at a temperature of 45°–50° C. An electromagnetic field of a strength that separates the strands of a duplex, but does not cause scission within a strand (e.g., a field imparting upon each magnetic bead an actual maximum force between about $5 \times 10^{-11}$ and $1 \times 10^{-9}$ N) is then applied for 15 seconds; then reversed for 5 seconds, and the solution is incubated at 45°–50° C. for two minutes. These electromagnetic pulse and incubation steps are then repeated about 20 times. The resulting 210 bp amplified product is then analyzed on gel electrophoresis.

EXAMPLE 7

Amplification of a Target DNA Sequence using MCR

An MCR reaction mixture was assembled containing 30 attomoles of linear lambda phage DNA (~100 pg) in a solution of 15 mM Tris HCl (pH 7.5), 12 mM MgCl$_2$, 50 mM NaCl, 1 mM dithiothreitol, 0.05 mM of each dNTP, 5% glycerol, 5% ethylene glycol, 0.1% TWEEN detergent, and 0.5 mM of each of two oligonucleotide primers. One of these primers was the magnetic primer, which is biotinylated at its 5' end and attached non-covalently to streptavidin-coated paramagnetic beads (DYNABEAD™). The nucleotide sequence of the magnetic primer was:

5'-CGAACAGGTTATCGAATTCAGCCAC-3'   (SEQ ID No.:3).

The other primer was the solid phase primer which is covalently attached by the 5' terminal phosphate group to the bottom of a well of a microtitre dish (Covalink, Nunc Inc., Napegrille, Ill.) comprising the reaction vessel in which MCR amplification was performed. The nucleotide sequence of the solid phase primer was:

5'-CATCGTCGTGTATTCCGGACAGTAC-3' (SEQ ID No.:4).

The MCR reaction mixture was heated to 94° C. for 1 min, cooled to 50° C. and 1–2 Units T7 DNA polymerase was added. Incubation at 50° C. was continued for about 1 min. The solution was then heated to 94° C. for about 1 min and cooled to 50° C. and placed into an MCR apparatus as described above.

1–2 Units of T7 DNA polymerase were added to the MCR reaction mixture and incubated at 45°–50° C. for the duration of the MCR amplification. An electromagnetic field generated by a solenoid of the MCR apparatus was applied for about 15 sec and then the polarity of the field was reversed for about 5 sec followed by incubation in the absence of the external magnetic filed for 5 sec. This cycle of electromagnetic pulses and incubations were repeated an additional 20 times. The resulting 750 bp DNA product was then eluted from the DYNABEADS™ in a solution of 90% formamide/10 mM EDTA and analyzed by gel electrophoresis. The results of such electrophoretic analysis confirmed amplification of a specific, 750 bp MCR product.

It should be understood that the foregoing disclosure emphasizes certain specific embodiments of the invention and that all modifications or alternatives equivalent thereto are within the spirit and scope of the invention as set forth in the appended claims.

We claim:

1. An apparatus for performing a magnetic cycle reaction, the apparatus comprising in combination:
   (a) a temperature-controlled sample block comprising a plate containing an array of a multiplicity of sample tube wells, wherein a portion of a sample tube fits within the sample tube well, and heating and cooling means in thermal contact with the sample block for controlling the temperature thereof;
   (b) a first magnetic element, wherein the first magnetic element is located above the sample block and in magnetic proximity thereof, wherein the first magnetic element comprises a multiplicity of coils, wherein the coils comprise a multiplicity of rams of an electricity-conducting wire around a soft iron core, and wherein the flow of electric current through the wire comprising the coil creates a magnetic field surrounding the first magnetic element which extends to the sample block;
   (c) a second magnetic dement, wherein the second magnetic element is located beneath the sample block and in proximity thereof, wherein the second magnetic element comprises a multiplicity of coils, wherein the coils comprise a multiplicity of turns of an electricity-conducting wire around a soft iron core, and wherein the flow of electric current through the wire comprising the coil creates a magnetic field surrounding the second magnetic element which extends to the sample block;
   (d) a controller comprising a microprocessor, wherein the controller is operatively linked to the temperature-controlled sample block and each of the first and second magnetic elements, wherein the controller is also operatively linked to a user interface and the controller controls electric current flow through each of the magnetic elements and the temperature of the temperature-controlled sample block; and
   (e) a power supply that is operatively linked to the controller and supplies electrical power to the apparatus.

2. A method for performing a magnetic cycle reaction to amplify a specific DNA fragment using the apparatus of claim 1, the method comprising:
   (a) incorporating into a nucleic acid strand complementary to the target nucleic acid a primer attached to a solid phase (solid phase primer) to create a solid phase strand bound to the target nucleic acid;
   (b) separating the solid phase strand and the target nucleic acid;
   (c) incorporating into a nucleic acid strand complementary to the solid phase strand a primer attached to a magnetic particle (magnetic primer) to yield a duplex having one solid phase strand and one magnetic strand;
   (d) separating the solid phase strand from the magnetic strand by applying an electromagnetic field of sufficient strength to dissociate the duplex, wherein said electromagnetic field is generated by the first magnetic element of the apparatus of claim 1;
   (e) allowing magnetic primers complementary to the solid phase strand to anneal to the solid phase strand by applying an electromagnetic field, wherein said electromagnetic field is generated by the second magnetic element of the apparatus of claim 1, and allowing solid phase primers complementary to the magnetic strand to anneal to the magnetic strand;
   (f) extending the annealed solid phase and magnetic primers with a suitable DNA polymerase; and
   (g) repeating steps (d) through (f) as many times as necessary to obtain a desired quantity of amplified DNA.

3. A method of amplifying a specific single stranded target nucleic acid using the apparatus of claim 1, the method comprising the steps of:
   (a) incorporating into a nucleic acid strand complementary to the target nucleic acid a magnetic primer to create a magnetic strand bound to the target nucleic acid by extending an annealed magnetic primer with a polymerase;
   (b) separating the magnetic strand and the target nucleic acid;
   (c) incorporating into a nucleic acid strand complementary to the magnetic strand a solid phase primer to yield a duplex having one solid phase strand and one magnetic strand by extending an annealed solid phase primer with a polymerase;
   (d) separating the solid phase strand from the magnetic strand by applying an electromagnetic field of sufficient strength to dissociate the duplex, by generating a magnetic field in the first magnetic element of the apparatus of claim 1;
   (e) allowing magnetic primers complementary to the solid phase strand to anneal to the solid phase strand by generating a magnetic field in the second magnetic element of the apparatus of claim 1, and allowing solid phase primers complementary to the magnetic strand to anneal to the magnetic strand;
   (f) extending the annealed solid phase and magnetic primers with a suitable DNA polymerase; and
   (g) repeating steps (d) through (f) as many times as necessary to obtain a desired quantity of amplified DNA.

4. A method of amplifying a specific double stranded target nucleic acid using the apparatus of claim 1, the method comprising the steps of:
   (a) separating the strands of the target nucleic acid to yield a first strand and a second strand;
   (b) incorporating a solid phase primer into a strand complementary to the first strand by extending an annealed solid phase primer with a polymerase, to yield a first heteroduplex having the first strand and a solid phase strand, and incorporating a magnetic primer into a strand complementary to the second strand by extending an annealed magnetic primer with a polymerase, to yield a second heteroduplex having the second strand and a magnetic strand;
   (c) separating the strands of the first heteroduplex and of the second heteroduplex;

(d) allowing magnetic primers complementary to the solid phase strand to anneal to the solid phase strand and allowing solid phase primers complementary to the magnetic strand to anneal to the magnetic strand;

(f) extending the annealed magnetic and solid phase primers with a DNA polymerase; and (g) separating the solid phase strand from the magnetic strand by applying an electromagnetic field of sufficient strength to dissociate the duplex, by generating a magnetic field in the first magnetic element of the apparatus of claim 1;

(h) allowing magnetic primers complementary to the solid phase strand to anneal to the solid phase strand by generating a magnetic field in the second magnetic element of the apparatus of claim 1, and allowing solid phase primers complementary to the magnetic strand to anneal to the magnetic strand;

(I) extending the annealed magnetic and solid phase primers with a DNA polymerase; and (j) repeating steps (g) through (I) as many times as necessary to obtain a desired quantity of amplified DNA.

* * * * *